(12) United States Patent
Anderson et al.

(10) Patent No.: US 11,413,048 B2
(45) Date of Patent: Aug. 16, 2022

(54) OCCLUSIVE MEDICAL DEVICE WITH DELIVERY SYSTEM

(71) Applicant: BOSTON SCIENTIFIC SCIMED, INC., Maple Grove, MN (US)

(72) Inventors: James M. Anderson, Corcoran, MN (US); Cass Alexander Hanson, Saint Paul, MN (US); David John Onushko, Minneapolis, MN (US); Jose A. Meregotte, Blaine, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 388 days.

(21) Appl. No.: 16/252,968

(22) Filed: Jan. 21, 2019

(65) Prior Publication Data

US 2019/0223883 A1 Jul. 25, 2019

Related U.S. Application Data

(60) Provisional application No. 62/619,388, filed on Jan. 19, 2018.

(51) Int. Cl.
*A61B 17/12* (2006.01)
*A61M 25/10* (2013.01)
*A61B 17/00* (2006.01)

(52) U.S. Cl.
CPC .. *A61B 17/12186* (2013.01); *A61B 17/12031* (2013.01); *A61B 17/12122* (2013.01);
(Continued)

(58) Field of Classification Search
CPC ................ A61B 17/0057; A61B 17/12; A61B 17/12022; A61B 17/12031;
(Continued)

(56) References Cited

U.S. PATENT DOCUMENTS 1,782,830 A    6/1876   French
1,967,318 A   10/1931   Monahan
(Continued)

FOREIGN PATENT DOCUMENTS

CN    106859722 A    6/2017
EP      0101012 A2   2/1984
(Continued)

OTHER PUBLICATIONS

PCT Search Report from co-pending Application PCT/US02/33808 dated May 20, 2003.
(Continued)

*Primary Examiner* — Robert A Lynch
(74) *Attorney, Agent, or Firm* — Seager, Tufte & Wickhem LLP

(57) ABSTRACT

An example medical device delivery system is disclosed. The delivery system includes an inflation shaft having a first lumen, a second lumen and a distal end region, the distal end region including an elongated tip. The delivery system also includes a detachment shaft extending along a portion of the inflation shaft. The delivery system also include a delivery shaft having a proximal end region, a distal end region and a lumen extending therein. The delivery system also includes an occlusive member positioned within at least a portion of the lumen of the delivery shaft, wherein the occlusive member is configured to expand and seal the opening of a left atrial appendage. Further, a portion of the elongated tip is removeably engaged with the occlusive member.

13 Claims, 12 Drawing Sheets

(52) U.S. Cl.
CPC ............ *A61B 17/12136* (2013.01); *A61B 2017/00495* (2013.01); *A61B 2017/00862* (2013.01); *A61B 2017/00898* (2013.01); *A61B 2017/1205* (2013.01); *A61B 2017/12054* (2013.01); *A61B 2017/12095* (2013.01); *A61M 2025/1054* (2013.01)

(58) Field of Classification Search
CPC .......... A61B 17/1205; A61B 17/12099; A61B 17/12109; A61B 17/12113; A61B 17/12122; A61B 17/12131; A61B 17/12136; A61B 2017/00623; A61B 2017/12054; A61B 17/12181; A61B 17/12186; A61B 17/1219; A61B 17/12195; A61M 25/0026; A61M 25/10; A61M 2025/0036; A61M 2025/0037; A61M 2025/004; A61M 2025/1052; A61M 2025/1054; A61M 2025/1061; A61M 2025/1072

See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,002,556 A | 3/1991 | Ishida et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halperin |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebrve |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,802 A | 1/1999 | Yoon et al. |
| 5,865,791 A | 2/1999 | Whayne et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |

(56) References Cited

U.S. PATENT DOCUMENTS

| | | | |
|---|---|---|---|
| 5,906,207 A | 5/1999 | Shen | |
| 5,910,154 A | 6/1999 | Tsugita et al. | |
| 5,911,734 A | 6/1999 | Tsugita et al. | |
| 5,916,236 A | 6/1999 | Muijs Van de Moer et al. | |
| 5,928,192 A | 7/1999 | Maahs | |
| 5,928,260 A | 7/1999 | Chin et al. | |
| 5,935,145 A | 8/1999 | Villar et al. | |
| 5,935,147 A | 8/1999 | Kensey et al. | |
| 5,935,148 A | 8/1999 | Villar et al. | |
| 5,941,249 A | 8/1999 | Maynard | |
| 5,944,738 A | 8/1999 | Amplatz et al. | |
| 5,947,997 A | 9/1999 | Pavcnik et al. | |
| 5,951,589 A | 9/1999 | Epstein et al. | |
| 5,951,599 A | 9/1999 | McCrory | |
| 5,954,694 A | 9/1999 | Sunseri | |
| 5,957,940 A | 9/1999 | Tanner et al. | |
| 5,961,545 A | 10/1999 | Lentz et al. | |
| 5,976,174 A | 11/1999 | Ruiz | |
| 5,980,514 A | 11/1999 | Kupiecki et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,993,483 A | 11/1999 | Gianotti | |
| 5,997,557 A | 12/1999 | Barbut et al. | |
| 6,004,348 A | 12/1999 | Banas et al. | |
| 6,007,523 A | 12/1999 | Mangosong | |
| 6,007,557 A | 12/1999 | Ambrisco et al. | |
| 6,010,517 A | 1/2000 | Baccaro | |
| 6,010,522 A | 1/2000 | Barbut et al. | |
| 6,013,093 A | 1/2000 | Nott et al. | |
| 6,024,754 A | 2/2000 | Engelson | |
| 6,024,755 A | 2/2000 | Addis | |
| 6,024,756 A | 2/2000 | Huebsch et al. | |
| 6,027,520 A | 2/2000 | Tsugita et al. | |
| 6,033,420 A | 3/2000 | Hahnen | |
| 6,042,598 A | 3/2000 | Tsugita et al. | |
| 6,048,331 A | 4/2000 | Tsugita et al. | |
| 6,051,014 A | 4/2000 | Jang | |
| 6,051,015 A | 4/2000 | Maahs | |
| 6,056,720 A | 5/2000 | Morse | |
| 6,063,070 A | 5/2000 | Eder | |
| 6,068,621 A | 5/2000 | Balceta et al. | |
| 6,074,357 A | 6/2000 | Kaganov et al. | |
| 6,076,012 A | 6/2000 | Swanson et al. | |
| 6,079,414 A | 6/2000 | Roth | |
| 6,080,182 A | 6/2000 | Shaw et al. | |
| 6,080,183 A | 6/2000 | Tsugita et al. | |
| 6,083,239 A | 7/2000 | Addis | |
| 6,096,053 A | 8/2000 | Bates | |
| 6,110,243 A | 8/2000 | Wnenchak et al. | |
| 6,124,523 A | 9/2000 | Banas et al. | |
| 6,132,438 A | 10/2000 | Fleischman et al. | |
| 6,135,991 A | 10/2000 | Muni et al. | |
| 6,136,016 A | 10/2000 | Barbut et al. | |
| 6,136,258 A * | 10/2000 | Wang | A61M 25/1029 264/514 |
| 6,139,527 A | 10/2000 | Laufer et al. | |
| 6,139,573 A | 10/2000 | Sogard et al. | |
| 6,152,144 A | 11/2000 | Lesh et al. | |
| 6,156,055 A | 12/2000 | Ravenscroft | |
| 6,161,543 A | 12/2000 | Cox et al. | |
| 6,171,329 B1 | 1/2001 | Shaw et al. | |
| 6,179,859 B1 | 1/2001 | Bates et al. | |
| 6,214,029 B1 | 4/2001 | Thill et al. | |
| 6,231,561 B1 | 5/2001 | Frazier et al. | |
| 6,231,589 B1 | 5/2001 | Wessman et al. | |
| 6,251,122 B1 | 6/2001 | Tsukernik | |
| 6,258,115 B1 | 7/2001 | Dubrul | |
| 6,270,490 B1 | 8/2001 | Hahnen | |
| 6,277,138 B1 | 8/2001 | Levinson et al. | |
| 6,290,674 B1 | 9/2001 | Roue et al. | |
| 6,319,251 B1 | 11/2001 | Tu et al. | |
| 6,328,727 B1 | 12/2001 | Frazier et al. | |
| 6,342,062 B1 | 1/2002 | Suon et al. | |
| 6,346,116 B1 | 2/2002 | Brooks et al. | |
| 6,364,895 B1 | 4/2002 | Greenhalgh | |
| 6,368,338 B1 | 4/2002 | Knya et al. | |
| 6,371,971 B1 | 4/2002 | Tsugita et al. | |
| 6,375,670 B1 | 4/2002 | Greenhalgh | |
| 6,391,044 B1 | 5/2002 | Yadav et al. | |
| 6,402,746 B1 | 6/2002 | Whayne et al. | |
| 6,419,669 B1 | 7/2002 | Frazier et al. | |
| 6,440,152 B1 | 8/2002 | Gainor et al. | |
| 6,443,972 B1 | 9/2002 | Bosma et al. | |
| 6,447,530 B1 | 9/2002 | Ostrovsky et al. | |
| 6,468,291 B2 | 10/2002 | Bates et al. | |
| 6,511,496 B1 | 1/2003 | Huter et al. | |
| 6,517,573 B1 | 2/2003 | Pollock et al. | |
| 6,547,760 B1 | 4/2003 | Samson et al. | |
| 6,551,303 B1 | 4/2003 | Van Tassel et al. | |
| 6,551,344 B2 | 4/2003 | Thill | |
| 6,558,405 B1 | 5/2003 | McInnes | |
| 6,562,058 B2 | 5/2003 | Seguin et al. | |
| 6,599,308 B2 | 7/2003 | Amplatz | |
| 6,652,555 B1 | 11/2003 | VanTassel et al. | |
| 6,652,556 B1 | 11/2003 | VanTassel et al. | |
| 6,689,150 B1 | 2/2004 | VanTassel et al. | |
| 6,730,108 B2 | 5/2004 | Van Tassel et al. | |
| 6,837,901 B2 | 1/2005 | Rabkin et al. | |
| 6,855,153 B2 | 2/2005 | Saadat | |
| 6,949,113 B2 | 9/2005 | Van Tassel et al. | |
| 6,994,092 B2 | 2/2006 | van der Burg et al. | |
| 7,011,671 B2 | 3/2006 | Welch | |
| 7,044,134 B2 | 5/2006 | Khairkhahan et al. | |
| 7,128,073 B1 | 10/2006 | van der Burg et al. | |
| 2001/0034537 A1 | 10/2001 | Shaw et al. | |
| 2002/0022860 A1 | 2/2002 | Borillo et al. | |
| 2002/0035374 A1 | 3/2002 | Borillo et al. | |
| 2002/0062133 A1 | 5/2002 | Gilson et al. | |
| 2002/0138094 A1 | 9/2002 | Borillo et al. | |
| 2002/0138097 A1 | 9/2002 | Ostrovsky et al. | |
| 2003/0023266 A1 | 1/2003 | Borillo et al. | |
| 2003/0057156 A1 | 3/2003 | Peterson et al. | |
| 2003/0181942 A1 | 9/2003 | Sutton et al. | |
| 2003/0220667 A1 | 11/2003 | van der Burg et al. | |
| 2004/0098031 A1 | 5/2004 | van der Burg et al. | |
| 2004/0215230 A1 | 10/2004 | Frazier et al. | |
| 2005/0004652 A1 | 1/2005 | van der Burg et al. | |
| 2005/0113861 A1 | 5/2005 | Corcoran et al. | |
| 2005/0203568 A1 | 9/2005 | Burg et al. | |
| 2005/0288706 A1* | 12/2005 | Widomski | A61M 25/10 606/213 |
| 2010/0222802 A1* | 9/2010 | Gillespie, Jr. | A61F 2/2481 606/192 |
| 2014/0100596 A1 | 4/2014 | Rudman et al. | |
| 2016/0106437 A1 | 4/2016 | Van Der Burg et al. | |
| 2016/0228126 A1* | 8/2016 | Squire | A61B 17/12113 |

FOREIGN PATENT DOCUMENTS

| | | |
|---|---|---|
| WO | 9313712 A1 | 7/1993 |
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |
| WO | 0115629 A1 | 3/2001 |
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |

(56) References Cited

FOREIGN PATENT DOCUMENTS

| WO | 03032818 A2 | 4/2003 |
| WO | 2016127078 A1 | 8/2016 |
| WO | 2018187732 A1 | 10/2018 |

OTHER PUBLICATIONS

PCT Search Report from PCT/US99/26325 dated Feb. 15, 2000.
Cragg et al; "Nonsurgical Placement of Arterial Endoprosthesis: A New Technique Using Nitinol Wire," Radiology vol. 147, No. 1 pp. 261-263, Apr. 1983.
Cragg et al; "A New Percutaneous Vena Cava Filter", ALJ, 141: 601-604, Sep. 1983.
Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.
Ruttenberg, Nonsurgical Therapy of Cardiac Disorders, Pediatric Consult, vol. 5, No. 2, pages not numbered, 1986.
Rashkind et al; Nonsurgical Closure of Patent Ductus Arteriosus: Clinical Application of the Rashkind PDA Occluder System, Circulation 75, No. 3, 583-592-1987.
Lock et al; "Transcatheter Umbrella Closure of Congenital Heart Defects," Circulation, vol. 75, No. 3, 593-599, 1987.
Lock et al; "Transcatheter Closure of Artrial Septal Defects," Circulation, vol. 79, No. 5 1091-1099, May 1989.
Wessel et al; "Outpatient Closure of the Patent Ductus Arteriosus," Circulation, vol. 77, No. 5 1068-1071, 1988.
Invite to Pay Additional Fees dated Feb. 22, 2019 for International Application No. PCT/US2018/066163.
International Search Report and Written Opinion dated Apr. 8, 2019 for International Application No. PCT/US2019/014409.

\* cited by examiner

OCCLUSIVE MEDICAL DEVICE WITH DELIVERY SYSTEM

CROSS-REFERENCE TO RELATED APPLICATIONS

This application claims the benefit of priority under 35 U.S.C. § 119 to U.S. Provisional Application Ser. No. 62/619,388, filed Jan. 19, 2018, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

This disclosure provides design, material, manufacturing method, and use alternatives for medical devices. An example medical device delivery system includes an inflation shaft having a first lumen, a second lumen and a distal end region, the distal end region including an elongated tip. The delivery system also includes a detachment shaft extending along a portion of the inflation shaft. The delivery system also include a delivery shaft having a proximal end region, a distal end region and a lumen extending therein. The delivery system also includes an occlusive member positioned within at least a portion of the lumen of the delivery shaft, wherein the occlusive member is configured to expand and seal the opening of a left atrial appendage. Further, a portion of the elongated tip is removeably engaged with the occlusive member.

Alternatively or additionally to any of the embodiments above, wherein the first lumen is radially offset from the second lumen.

Alternatively or additionally to any of the embodiments above, wherein the inflation shaft includes a central longitudinal axis, and wherein the elongated tip is radially offset relative to the longitudinal axis.

Alternatively or additionally to any of the embodiments above, wherein a portion of the tip member includes a circular cross-sectional shape.

Alternatively or additionally to any of the embodiments above, wherein the distal end region of the inflation shaft has a first aperture aligned with the first lumen and a second aperture aligned with the second lumen, and wherein the first aperture is positioned distal to the second aperture.

Alternatively or additionally to any of the embodiments above, wherein the delivery shaft includes a third aperture extending through a wall of the delivery shaft, and wherein the third aperture is configured to radially align with the second aperture.

Alternatively or additionally to any of the embodiments above, wherein the occlusive member includes a valve, and wherein a portion of the tip member is releaseably engaged with a portion of the valve.

Alternatively or additionally to any of the embodiments above, wherein the tip member is configured to extend through the valve and into an inflation cavity of the occlusive member.

Alternatively or additionally to any of the embodiments above, wherein the inflation shaft is configured to translate relative to the occlusive member such that the first lumen, the second lumen or both the first lumen and second lumen are in fluid communication with an inflation cavity of the occlusive member.

Alternatively or additionally to any of the embodiments above, wherein the first lumen is configured to permit a first fluid to be injected into the inflation cavity of the occlusive member and wherein the second lumen is configured to permit a second fluid to be injected into the inflation cavity of the occlusive member, and wherein the first fluid is configured to combine with the second fluid.

Alternatively or additionally to any of the embodiments above, wherein the first fluid includes blood and wherein the second fluid includes fibrin.

Alternatively or additionally to any of the embodiments above, wherein both the inflation shaft and the detachment shaft extend within a portion of the lumen of the delivery shaft.

Alternatively or additionally to any of the embodiments above, wherein the detachment shaft includes a lumen extending therein and wherein the inflation shaft extends within a portion of the lumen of the detachment shaft.

Alternatively or additionally to any of the embodiments above, wherein the detachment shaft is configured to contact a distal end region of the occlusive member while the inflation shaft is removed from the occlusive member.

Another example medical device delivery system for occluding the left atrial appendage includes:

an inflation shaft having a first lumen, a second lumen and a distal end region, the distal end region including an elongated tip; and an expandable balloon coupled to the inflation shaft, wherein the balloon includes an inner expansion cavity;

wherein the inflation shaft is configured to inject a first material into the expansion cavity;

wherein the inflation shaft is configured to inject a second material into the expansion cavity;

wherein the first material combines with the second material within the expansion cavity to form a semi-solid material, and wherein the semi-solid material is configured to expand the balloon within the opening of the left atrial appendage.

Alternatively or additionally to any of the embodiments above, wherein the first lumen is radially offset from the second lumen.

Alternatively or additionally to any of the embodiments above, the inflation shaft includes a central longitudinal axis, and wherein the elongated tip is radially offset relative to the longitudinal axis.

Alternatively or additionally to any of the embodiments above, wherein the first material includes blood and wherein the second material includes fibrin.

Alternatively or additionally to any of the embodiments above, wherein the semi-solid material is designed to biodegrade over a time period.

An example method for sealing the left atrial appendage includes:

advancing a medical device delivery system to a position adjacent the left atrial appendage, wherein the delivery system includes:
- an inflation shaft having a first lumen, a second lumen and a distal end region, the distal end region including an elongated tip;
- a detachment shaft extending along a portion of the inflation shaft;
- a delivery shaft having a proximal end region, a distal end region and a lumen extending therein; and
- an occlusive member positioned within a portion of the lumen of the delivery shaft;

inserting a portion of the inflation shaft into an inflation cavity of the occlusive member such that the first lumen and the second lumen are in fluid communication with an inflation cavity;

injecting a first fluid into the inflation cavity of the occlusive member;

injecting a second fluid into the inflation cavity such that it combines with the second fluid;

removing the inflation shaft from the occlusive member.

The above summary of some embodiments is not intended to describe each disclosed embodiment or every implementation of the present disclosure. The Figures, and Detailed Description, which follow, more particularly exemplify these embodiments

BRIEF DESCRIPTION OF THE DRAWINGS

The disclosure may be more completely understood in consideration of the following detailed description of various embodiments in connection with the accompanying drawings, in which.

Figure 1:
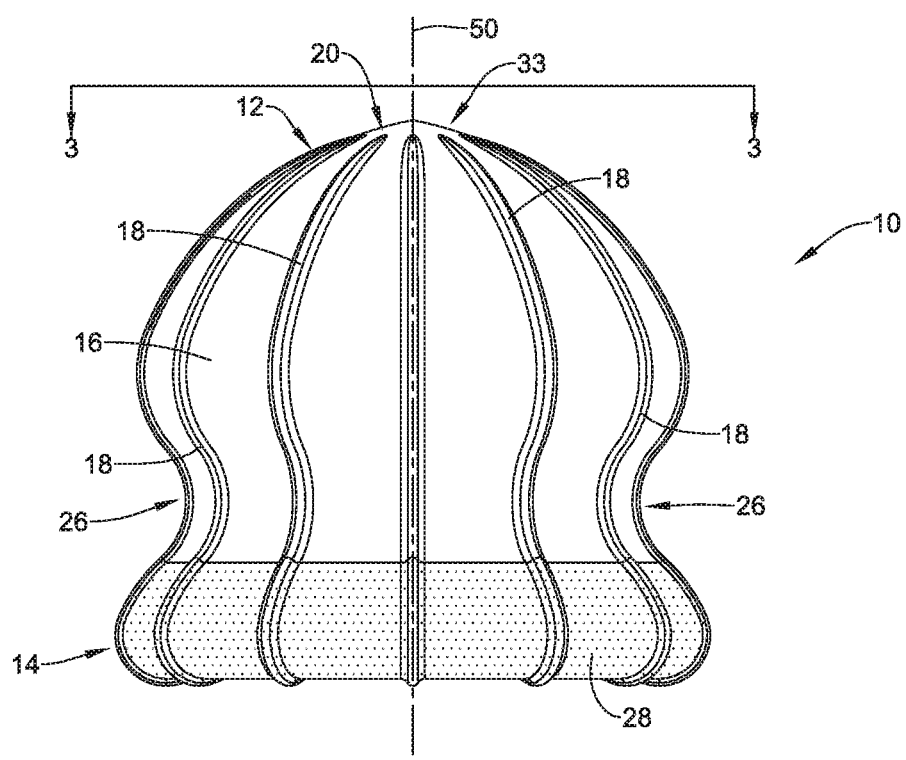
FIG. 1 is a plan view of an example occlusive member.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive members that close off the left atrial appendage from the heart and/or circulatory system, thereby lowering the risk of stroke due to thrombolytic material entering the blood stream from the left atrial appendage. Example occlusive members that close off the left atrial appendage and medical device delivery systems utilized to position the occlusive members are disclosed herein.

FIG. 1 illustrates an example occlusive member 10. The occlusive member 10 may include a first end region 12 and a second end region 14. As will be discussed in greater detail below, the first end region 12 may include the portion of the occlusive member 10 which extends farthest into a left atrial appendage, while the second end region may include the portion of the occlusive member 10 which is positioned closer to an opening of the left atrial appendage.

The occlusive member 10 may include an expandable member 16. The expandable member 16 may also be referred to as an expandable balloon 16. The expandable member 16 may be formed from a highly compliant material (e.g., "inflation material") which permits the expandable member 16 to expand from a first unexpanded (e.g., deflated, collapsed) configuration to a second expanded (e.g., inflated) configuration. In some examples, the expandable member 16 may be inflated to pressures from about 4 psi to 200 psi. It can be appreciated that the outer diameter of the occlusive member 10 may be larger in the expanded configuration versus the unexpanded configuration.

In some examples, the expandable member 16 may be constructed from silicone or a low-durometer polymer, however, other materials are contemplated. Additionally, the expandable member 16 may be impermeable to blood and/or other fluids, such as water. In some embodiments, the expandable member 16 may include a woven, braided and/or knitted material, a fiber, a sheet-like material, a metallic or polymeric mesh, or other suitable construction. Further, in some embodiments, the expandable member 16 may prevent thrombi (e.g., blood clots, etc.) originating in the left atrial appendage from passing through the occlusive member 10 and into the blood stream. Further, in some instances the occlusive member 10 may promote endothelial growth after implantation, thereby effectively removing the left atrial appendage from the patient's circulatory system. Some suitable, but non-limiting, examples of materials for the occlusive member 10 are discussed below.

FIG. 1 further illustrates that occlusive member 10 may include one or more spine members 18 extending along the longitudinal axis 50 of the expandable member 16 from the second end region 14 to the first end region 12. In some examples disclosed herein, the spine members 18 may be described as positioning members 18. Each of the spine members 18 may include a first end 20 and a second end 22 (shown in FIG. 2). FIG. 1 further illustrates that the each of the individual spine members 18 may be spaced apart from adjacent spine members 18. In other words, the spacing between adjacent spine members 18 may be substantially uniform around the circumference of the expandable member 16. In some examples, the spine members 18 may include one or more materials which are stiffer, higher durometer materials than the material from which the expandable member 16 is constructed. Some suitable, but non-limiting, examples of materials for the spine members 18 are discussed below.

However, it is contemplated that in some instances the spacing between spine members 18 may not be uniform. In some examples, the spacing between adjacent spine members 18 may be variable (e.g., non-uniformly spaced) around the circumference of the expandable member 16. Additionally, it is contemplated that the spine members 18 may form a framework in which the spine members 18 are connected to one another via a series of laterally extending members. A variety of different geometries for example frameworks are contemplated.

As illustrated in FIG. 1, the first end region 12 of the expandable member 16 may extend radially inward to form an apex region 33. Additionally, as shown in FIG. 1, each of the first end portions 20 of each of the spine members 18 may extend inward along the longitudinal axis 50 toward the apex region 33 of the expandable member 16.

Additionally, FIG. 1 illustrates that the occlusive member 10 may include a "nesting region" 26. The nesting region 26 may include a portion of the occlusive member 10 which is configured to nest within an opening of the left atrial appendage (as is illustrated and described further in FIG. 5). The nesting region 26 may include a portion of the occlusive member 10 which extends radially inward toward the longitudinal axis 50 of the occlusive member 10. Further, the inward curve which defines the nesting region 26 may extend circumferentially around the occlusive member 10. In other words, the inward curvature of the nesting region 26 may resemble a channel or groove which extends around the circumference of the occlusive member 10.

FIG. 1 further illustrates that the second end region 28 of the occlusive member 10 may include a coating 28. The coating 28 may extend around the circumference of the occlusive member 10 (including both the expandable member 16 and the spine members 18). In some examples, the coating 28 may promote cellular growth along the surface thereof. For example, the coating 28 may include elements with promote endothelial growth along the surface thereof. For example, the endothelial growth elements may accelerate the ability for endothelial cellular tissue to form a seal across an opening of the left atrial appendage.

Figure 2:
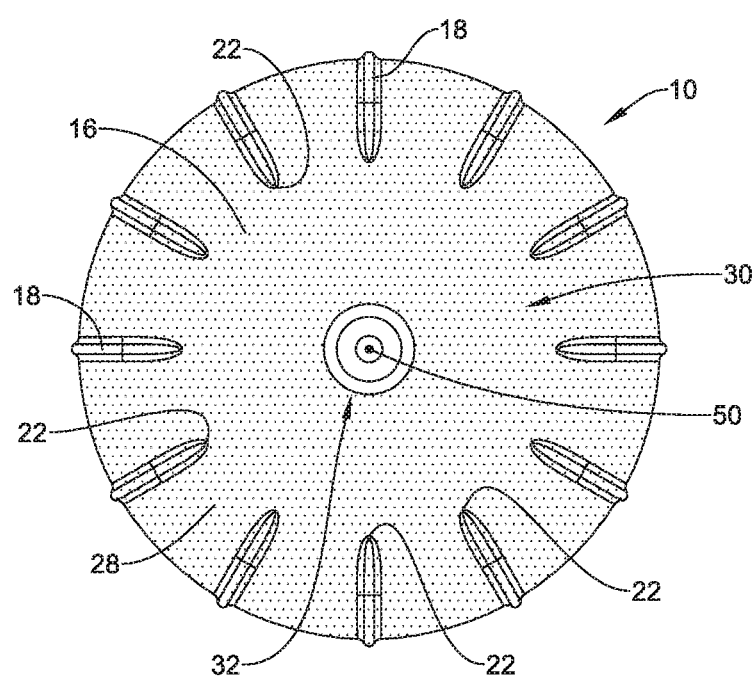
FIG. 2 shows a bottom view of the occlusive member of FIG. 1.

FIG. 2 illustrates a bottom view of the occlusive device described in FIG. 1. FIG. 2 illustrates that the occlusive device may include a bottom surface 30. As discussed above, the second end regions 22 of the spine members 18 may "wrap" along the second end region 14 (shown in FIG. 1) and terminate on the bottom surface 30.

FIG. 2 shows twelve spine members 18 positioned circumferentially around the longitudinal axis 50 of the occlusive member 10. However, while FIG. 2 illustrates twelve spine members 18 positioned around the longitudinal axis 50 of the occlusive member 10, it is contemplated that greater or less than twelve spine members 18 may be utilized for any example occlusive members 10 contemplated herein. For example, occlusive member 10 may include 1, 2, 3, 4, 5, 6, 7, 8, 9, 10, 11, 12, 13, 14, 15 or more spine members 18 positioned along occlusive member 10.

As will be described in greater detail below, FIG. 2 illustrates a valve member 32 positioned in a central region of the bottom surface 30 of the occlusive member 10. The valve 32 may be utilized as an access aperture to insert a secondary medical device (not shown). The secondary medical device may be utilized to inject a liquid material into the expandable member 16. FIG. 2 further illustrates that the coating 28 may be positioned along the bottom surface 30 of the occlusive member 10. The coating 28 may cover all or a portion of the bottom surface 30 of the occlusive member 10.

Figure 3:
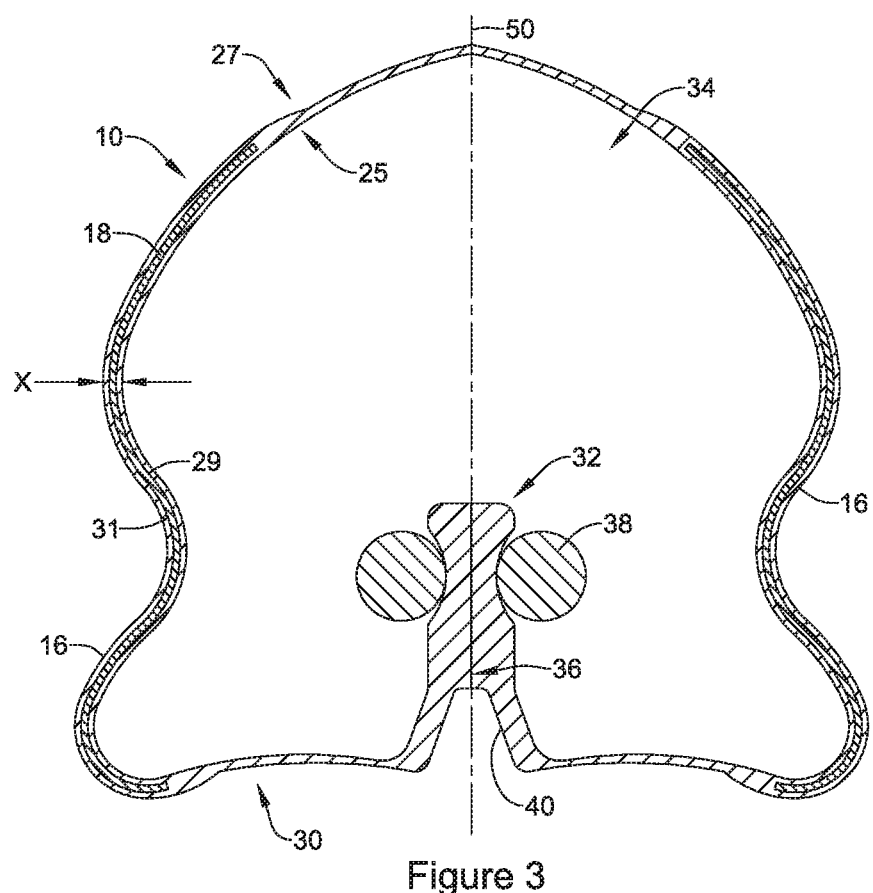
FIG. 3 shows a cross-sectional view along line 3-3 of FIG. 1.

FIG. 3 shows a cross-sectional view along line 3-3 of FIG. 1. FIG. 3 illustrates that the expandable member 16 may include an inner surface 25 and an outer surface 27. Additionally, FIG. 3 shows that the expandable member 16 may include a wall thickness "X" defined as width of the wall between the inner surface 25 and the outer surface 27 of the expandable member 16.

FIG. 3 further illustrates that the spine members 18 may be positioned within the wall of the expandable member 16. FIG. 2 illustrates that each of the spine members 18 may include an inwardly-facing surface 29 and an outwardly-facing surface 31. The inner surface 29 of each of the spine members 18 may be positioned radially outward of the inner surface 25 of the expandable member 16. Further, the outer surface 31 of each of the spine members 18 may be positioned radially inward of the outer surface 27 of the occlusive member 10. In other words, each of the spine members 18 may be embedded (e.g., encased, surrounded, etc.) within the wall of the expandable member 16. However, this is not intended to be limiting. Rather, it can be appreciated that in some examples a portion of one or more of the spine members 18 may extend radially away from the outer surface 27 of the expandable member 16. For example, in some instances a portion of the outer surface 31 of one or more of the spine members 18 may be free from the expandable member 16.

FIG. 3 further illustrates that the expandable member 16 may include an inner cavity 34. The inner cavity 34 may be referred to as an inflation cavity. The inflation cavity 34 may be described as a chamber in which in an inflation material (e.g., media, liquid, gas, etc.) may be inserted (via valve 32, for example) in order to expand the expandable member 16. As will be described in greater detail below, as an inflation media is inserted into the expandable member 16, the inner cavity may expand, thereby permitting the expandable member 16 to seal against the tissue walls defining an opening in the left atrial appendage.

As stated above, inflation of the inflation cavity 34 may be accomplished by inserting inflation material through the valve 32. As shown in FIG. 2, the valve 32 may be formed from the same material that forms the wall of the expandable member 16. In other words, the valve 32 may be an extension of the wall of the expandable member 16. Additionally, as illustrated in FIG. 3, the valve 32 may be positioned within the inflation cavity 34. For example, FIG. 3 illustrates that the valve 32 may extend (e.g., project) into the inflation cavity 34 from the bottom surface 30.

The valve 32 may include an inflation lumen 36 which may be designed to allow a secondary medical device to be inserted therethrough. As shown in FIG. 3, the inflation lumen 36 may be aligned with the longitudinal axis 50 of the occlusive member 10. FIG. 3 shows the inflation lumen 36 in a closed configuration such that it would prevent inflation media (not shown in FIG. 3) from passing back through the valve 32. As shown in FIG. 3, in some examples the valve 32 may be maintained in a closed configuration via a torus-shaped mechanical gasket 38. For simplicity purposes, gasket 38 will be referred to as an "O-ring" below.

It can be appreciated that the O-ring 38 may be formed from a material (e.g., rubber, elastomer, etc.) which permits it to compress radially inwardly. As shown in FIG. 3, the O-ring may be positioned around the valve 32 such that the O-ring 38 compresses and closes the lumen 36 of the valve 32. However, the O-ring 38 must also permit the lumen 36 to radially expand such that a secondary medical device may be inserted therethrough (for inflation of the expandable member 16 as described above). Therefore, in some examples the O-ring 38 may designed to stretch and allow an inflation device access to the inflation cavity 34 while also exerting sufficient radially inward force to maintain the lumen 36 in a closed configuration once the inflation cavity 34 has been inflated and the inflation device (not shown in FIG. 3) is removed from the lumen 36 (inflation of the inflation cavity 34 will be discussed with respect to FIGS. 8-12).

As will be discussed in greater detail below, the occlusive member 10 may be coupled to a delivery system in a variety of ways. Further, a component of a delivery system may also function as a secondary medical device utilized to inflate the expandable member 16. FIG. 3 illustrates an attachment region 40 which may be utilized to attach a component of a delivery system to the occlusive member 10. The attachment region 40 may include a variety of features which permit attachment to a delivery system. For example, the attachment region 40 may include threads which mate with a threaded region on a component of a medical device system (not shown in FIG. 3). In other examples, the attachment region 40 may be designed such that it forms a "press-fit" with a distal end region of a component of a medical device system.

Figure 4:
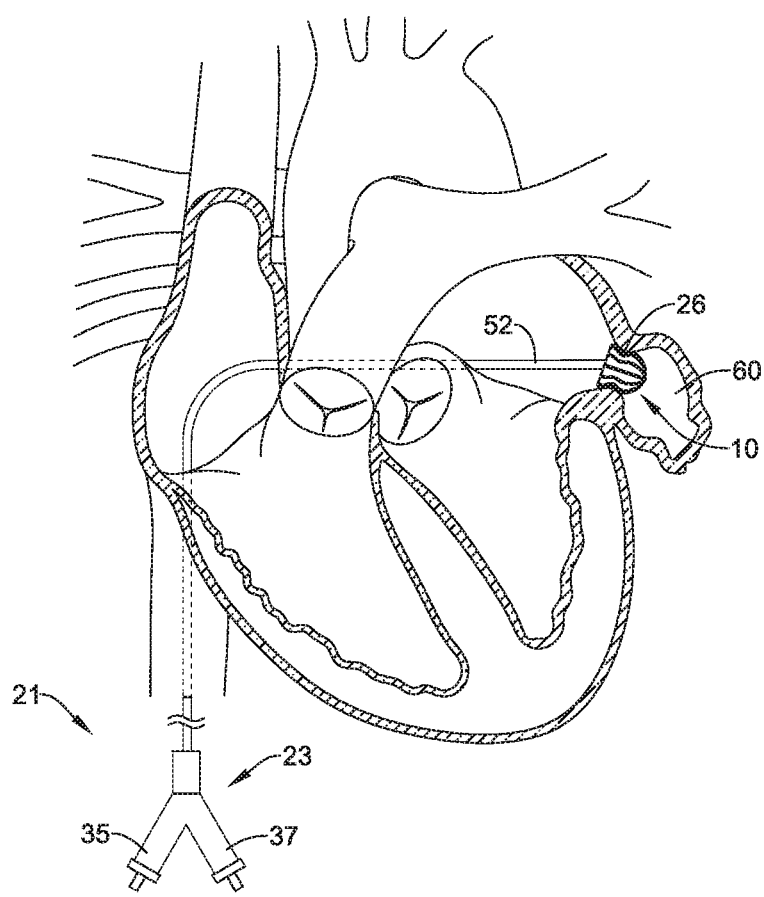
FIG. 4 shows an example occlusive member positioned in an opening of the left atrial appendage.

FIG. 4 illustrates that the occlusive member 10 may be inserted and advanced through a body lumen via an occlusive member delivery system 21. FIG. 4 further illustrates the occlusive member 10 positioned within the left atrial appendage 60. As discussed above, in some instances the occlusive member 10 may be positioned within the left atrial appendage 60 such that the nesting region 26 is nested within a portion of the left atrial appendage 60.

In some instances, the occlusive member delivery system 21 may include one or more catheter components (not shown in FIG. 4) which extend within a lumen of the delivery shaft 52. The delivery shaft 52 (and the components extending therein) may be guided toward the left atrium via various chambers and lumens of the heart (e.g., the superior vena cava, the inferior vena cava, the right atrium, etc.) to a position adjacent the left atrial appendage 60.

The occlusive member delivery system 21 may include a hub 23 coupled to a proximal region of the delivery shaft 52. The hub 23 may be manipulated by a clinician to direct the distal end region of the delivery shaft 52 to a position adjacent the left atrial appendage 60. In some examples, a proximal end of the occlusive member 10 may be designed to releasably attach, join, couple, engage, or otherwise connect to the distal end of the delivery shaft 52. For example, in some embodiments, an end region of the occlusive member 10 may include a threaded insert coupled thereto.

In at least one example contemplated herein, one or more components of the delivery system 21 may be designed to releasably attach, join, couple, engage, or otherwise connect to the distal end of the occlusive member 10 via a press fit. Further, as will be discussed in greater detail below, one or more components of the delivery system 21 may include multiple lumens which permit one or more materials to be inserted into the inflation cavity 34 of the occlusive member 10. It can be appreciated that first connection port 35 and the second connection port 37 of the hub 23 may provide fluid access to a first lumen and a second lumen, respectively, of a tubular inflation shaft extending within the delivery shaft 52.

Figure 5:
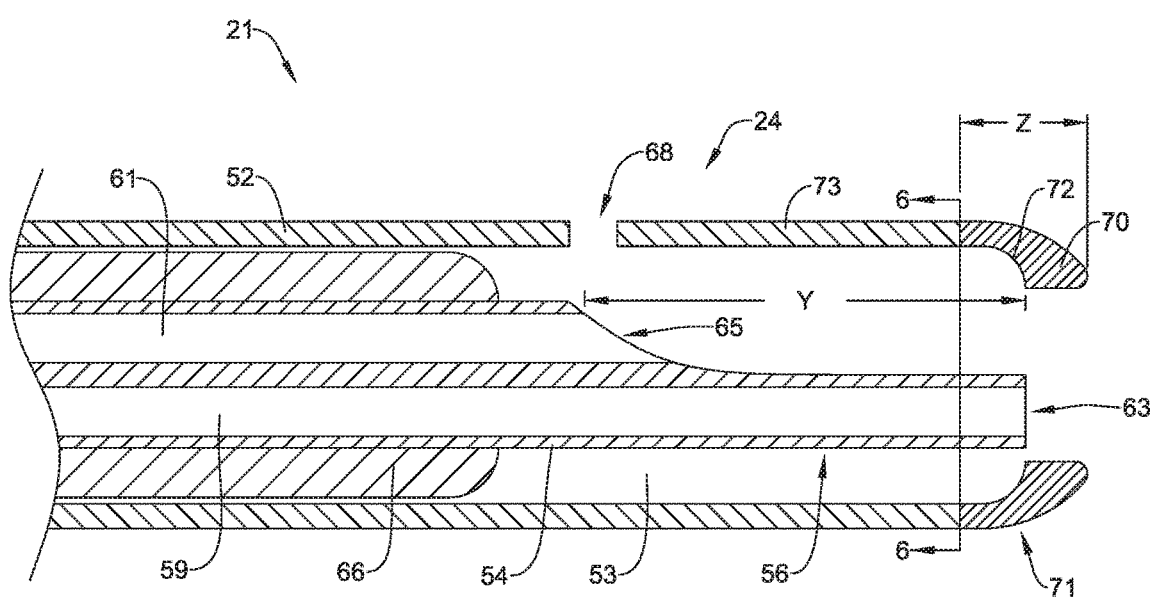
FIG. 5 shows a cross-sectional view of an example component of a medical device delivery system.

FIG. 5 illustrates the distal end region 24 of the delivery system 21 described above. Specifically, FIG. 5 illustrates the distal end region of the delivery shaft 52 which may be utilized to advance and position the occlusive member 10 adjacent the left atrial appendage prior to deployment of the occlusive member 10 (for simplicity purposes, FIG. 5 omits occlusive member 10 from the illustration). FIG. 5 further illustrates that the delivery system 21 may include an inflation shaft 54 positioned within a lumen 53 of the delivery shaft 52. Additionally, FIG. 5 illustrates that the delivery system 21 may include a detachment shaft 66 positioned within the lumen 53 of the delivery shaft 52. In some instances, the delivery shaft 52 may include a lubricious liner extending along its inner surface. The lubricious liner may be constructed from a polymeric material such as PTFE, HDPE or the like.

In some examples the detachment shaft 66 may extend proximally and engage with the hub 23. Additionally, in some instances the detachment shaft 66 may include an outer layer of material (e.g., polymer, PU, silicone, etc.) which may provide a fluid-tight seal between the outer surface of the detachment shaft 66 and the inner surface of the delivery shaft 52. Further, FIG. 5 illustrates that the inflation shaft 54 may extend within a lumen of the detachment shaft 66. As will be described and illustrated below, each of the inflation shaft 54, the detachment shaft 66 and the delivery shaft 52 may translate longitudinally relative to one another.

The inflation shaft 54 shown in FIG. 5 may include a first lumen 59 and a second lumen 61 extending therein. The inflation shaft 54 may extend proximally within the lumen 53 of the delivery shaft 52 and engage (e.g., attach) to the hub member 23. In some examples, the first lumen 59 may be fluidly aligned with the first connection port 35 and the second lumen 61 may be fluidly aligned with the second connection port 37 of the hub member 23. In other words, a clinician may inject a first material into the first lumen 59 via the first connection port 35 and inject a second material into the second lumen 61 via the second connection port 37.

FIG. 5 further illustrates that each of the first lumen 59 and the second lumen 61 may include a distal aperture positioned at the end of the first lumen 59 and the second lumen 61, respectively. Specifically, the inflation shaft 54 may include a first distal aperture 63 positioned at the end of the first lumen 59 and a second distal aperture 65 positioned at the end of the second lumen 61. Each of the first distal aperture 63 and the second distal aperture 65 may be aligned with the first lumen 59 and the second lumen 61, respectively.

FIG. 5 further illustrates that the inflation shaft 54 may include a tip 56 extending distally within the lumen 53 of the delivery shaft 52. As shown in FIG. 5, the tip 56 may be offset from a central, longitudinal axis of the inflation shaft 54. In other words, the tip 56 may lengthen the first lumen 59 of the inflation shaft 54. Accordingly, FIG. 5 further illustrates that the first distal aperture 63 and the second distal aperture 65 may be spaced apart from one another a distance depicted as "Y" in FIG. 5. In some examples, the distance "Y" may be from about 2 mm to about 20 mm, or about 2.5 mm to about 10 mm, or about 3 mm to about 6 mm, or about 4.5 mm.

As shown in FIG. 5, the distal end 71 of the delivery shaft 52 may include a radiopaque portion. The radiopaque portion of the distal end 71 of the delivery shaft 52 is depicted by dimension "Z" in FIG. 5. This portion of the tip may include an expandable, elastomeric, non-reinforced material. As will be discussed in greater detail below, utilizing an expandable material may be beneficial to allow the distal end 71 of the delivery shaft 52 to permit the inflation shaft 54 and/or the detachment shaft 66 to pass through the distal end 71 of the delivery shaft 52. Example materials utilized to create the radiopaque portion of the tip may include 35D Pebax or polyurethane loaded with tungsten, bismuth and/or barium. Some suitable, but non-limiting, examples of materials for the radiopaque portion of the tip are discussed below.

Additionally, the distal end 71 of the delivery shaft 52 may include a narrowed portion 70. The narrowed portion 70 of the lumen 53 of the delivery shaft 52 may include an inner diameter which is less than a more distal portion of the lumen 53. In other words, FIG. 5 illustrates while the outer diameter of the delivery shaft 52 may remain constant, the wall 73 may thicken (extend radially inward) at the narrowed portion 70 of the distal end 71 of the delivery shaft 52. The increased wall thickness may create a decreased inner diameter along the narrowed portion 70 of the delivery shaft 52. Further, FIG. 5 illustrates that the distal end 71 may include a curved transition portion 72 which curves radially inward along the distal end 71 of the delivery shaft 52. As will be discussed in greater detail below, the narrowed portion 70 of the distal end 71 may prohibit the occlusive member (not shown in FIG. 5) from pre-maturely deploying out of the distal end 71 of the delivery shaft 52.

FIG. 5 further illustrates that that delivery shaft 52 may include an inflow aperture 68 extending radially inward through the wall 73. As will be described in greater detail below, the inflow aperture 68 may be aligned with the second distal aperture 65 of the inflation shaft 54. It can be appreciated that in some examples, bodily fluids (e.g., blood) positioned adjacent the inflow aperture 68 may be drawn through the inflow aperture 68 and into the second lumen 61 if a vacuum (e.g., suction) is applied through the second lumen 61. For example, a clinician may attach a syringe to the second connection port 37 (which is in fluid communication with the second lumen 61) and draw a vacuum within the second lumen 61. The vacuum applied to the second lumen 61 may draw blood through the inflow aperture 68, the second distal aperture 65 and into the second lumen 61. The clinician may then inject the blood positioned with the second lumen 61 out of the lumen after translating the inflation shaft 54 within the lumen 53 of the delivery shaft 52.

Figure 6:
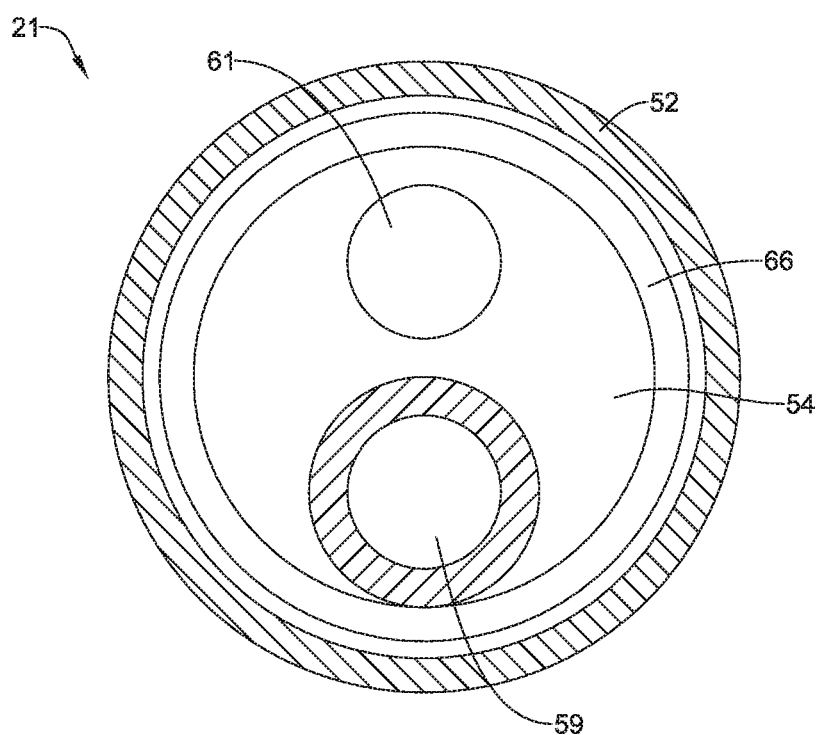
FIG. 6 shows an end view of the example component shown in FIG. 5.

FIG. 6 is a cross-sectional view along line 6-6 of FIG. 5. FIG. 6 shows the inflation shaft 54 including the first lumen 59 and the second lumen 61. It can be appreciated from FIG. 6 that the first lumen 59 may be spaced away from the second lumen 61. In other words, the first lumen 59 (which extends distally through the tip 56 shown in FIG. 5), may be offset from a central longitudinal axis of the inflation shaft 54. While FIG. 6 illustrates that both the first lumen 59 and the second lumen 61 may be substantially circular, this is not intended to be limiting. Rather, the first lumen 59 and the second lumen 61 may be oval, square, triangular, rectangular or other similarly shapes. FIG. 6 further illustrates that that inflation shaft 54 may extend within a lumen of the detachment shaft 66. Additionally, FIG. 6 also illustrates both the inflation shaft 54 and the detachment shaft 66 positioned within the lumen of the delivery shaft 52.

Figure 7:
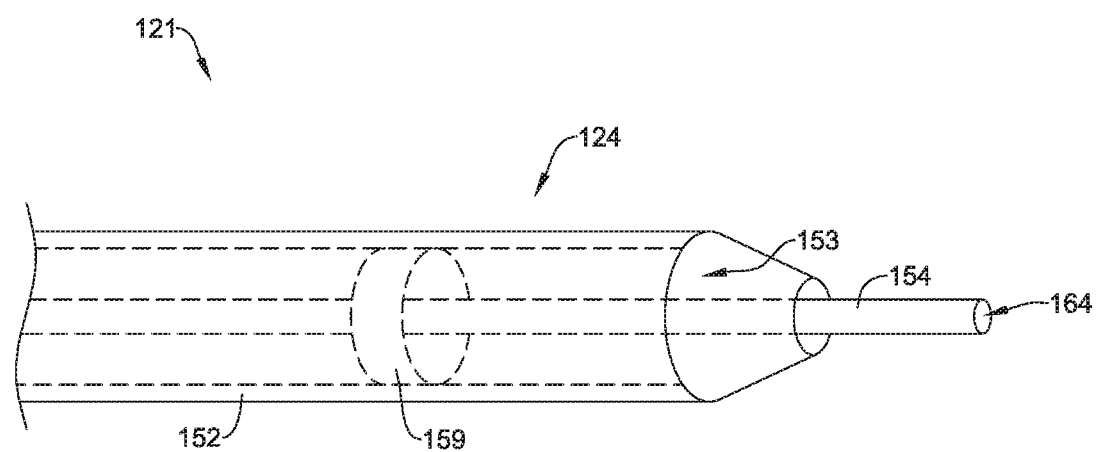
FIG. 7 shows another example component of a medical device delivery system.

FIG. 7 illustrates the distal end region 124 of another example delivery system 121. As illustrated in FIG. 7, the distal end region 124 of the delivery system 121 may include a delivery shaft 152. The delivery shaft 152 may be a tubular member including a lumen 153 extending therein. As shown in FIG. 7, the distal end region of the delivery shaft 152 may include a tapered portion. Additionally, the delivery system 121 may include an inflation shaft 154. The inflation shaft 154 may include a lumen 164. It can be appreciated that the inflation shaft 154 may extend proximally within the lumen 153 of the delivery shaft 152 and engage (e.g., attach) to the hub 23 (described above). Further, the lumen 164 of the inflation shaft 154 may be fluidly aligned with the first connection port 35 and the lumen 153 of the delivery shaft 152 may be fluidly aligned with the second connection port 37 of the hub member 23. In other words, a clinician may inject a first material into the lumen 164 via the first connection member 35 and inject a second material into the lumen 153 via the second connection member 37.

It can be further appreciated from FIG. 7 that the inflation shaft 154 and/or the delivery shaft may extend proximally and couple (e.g., attach) to the hub member 23. Additionally, it can be appreciated that the inflation shaft 154 may translate longitudinally with respect to the delivery shaft 152. Additionally, FIG. 7 illustrates that the delivery system 121 may include a stopper 159 positioned within the lumen 153 of the delivery shaft 152. Further, inflation shaft 154 may extend through the stopper 159. It can be appreciated that as the inflation shaft 154 is translated within the lumen 153 of the delivery shaft 152, the stopper 159 may create a suction to draw bodily fluids (e.g., blood) into the lumen 153 and may also push material out of the lumen 153 when translated in a proximal-to-distal direction.

FIGS. 8-12 illustrate the example occlusive member 10 (described above) being positioned and deployed via the delivery system 21 in an opening of the left atrial appendage 60. As discussed above, in some examples, the occlusive member 10 may be configured to shift between a collapsed configuration and an expanded configuration. For example, in some instances, the occlusive member 10 may be in a collapsed configuration during delivery via an occlusive device delivery system, whereby the occlusive member 10 expands to an expanded configuration once deployed from the occlusion implant delivery system.

As discussed above, in some instances it may be desirable to inject one or more materials (e.g., fluids, gels, bodily fluids, etc.) into an occlusive device to expand it from a collapsed configuration to an expanded configuration. Further, in some examples it may be desirable to combine (e.g., mix, etc.) one or more materials within an occlusive device. Further, in some instances one or more fluids may be combined (e.g., mixed) to form a semi-solid substance (e.g., a gel-like substance). For example, in some instances it may be desirable to combine blood (or similar fluid) with fibrin and/or thrombin (or similar fluid) to form a semi-solid substance within the expansion cavity of the occlusive device. In some instances, when blood and fibrin are combined (e.g., mixed) within the inflation cavity they may create a compliant, semi-solid occlusive "plug" which seals the opening to the left atrial appendage. Utilizing a semi-solid material to form the seal to the left atrial appendage may be beneficial because it may mold itself to the specific anatomical shape of the opening to the left atrial appendage. Further, in some instances, the semi-solid substance formed from the blood and fibrin mixture may be designed to biodegrade after a predetermined time period. The following figures disclosed a method of combining blood (surrounding the left atrial appendage) with injected fibrin to form a semi-solid material within the inflation cavity of the occlusive member 10.

Figure 8:
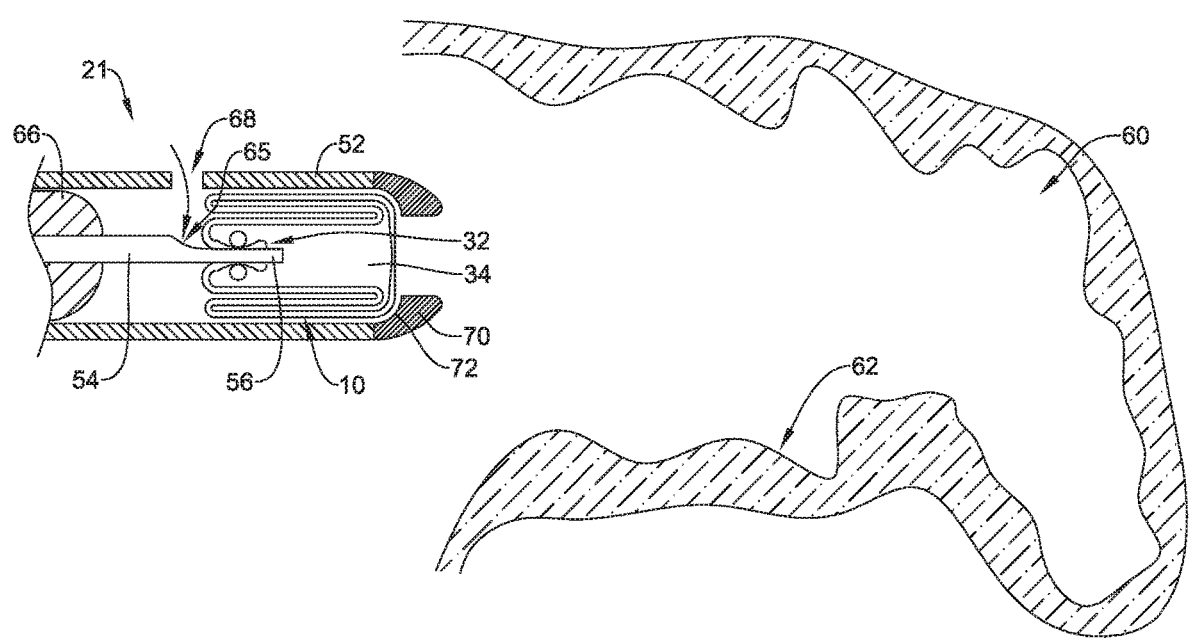
FIGS. 8-12 show an example occlusive member being positioned within an opening of the left atrial appendage.

FIG. 8 shows the occlusive member 10 positioned in a collapsed state within the delivery shaft 52 of the delivery system 21. It can be appreciated from FIG. 8 that the distal end of the delivery system 21 has been advanced to a position adjacent the opening to the left atrial appendage 60. Further, FIG. 8 illustrates that the occlusive member 10 may be detachably coupled to the inflation shaft 54 of the delivery system 21. For example, FIG. 8 illustrates that the tip 56 of the inflation shaft 54 may be partially inserted (e.g., press fit) into the valve 32 of the occlusive member 10.

The occlusive member 10 shown in FIG. 8 may be described as being in a deflated or delivery configuration. In other words, the occlusive member 10 may not contain any inflation media within its inflation cavity 34. It can be appreciated that it may be desirable to maintain the occlusive member 10 in a collapsed configuration when delivering the occlusive member 10 to the target site (e.g., an opening in the left atrial appendage). A collapsed configuration may permit the occlusive member 10 to more easily track through tortuous vasculature as a clinician directs the device to the target site.

FIG. 8 further illustrates that the occlusive member 10 may be positioned adjacent to the curved portions 72 of the narrowed portion 70 of the delivery shaft 52. It can be appreciated that the narrowed portion 70 may be designed to prevent the occlusive member 10 from prematurely deploying out of the delivery shaft 52. As will be described in greater detail below, the occlusive member 10 may be advanced out of the delivery shaft 52 when the detachment shaft 66 and the inflation shaft 54 are advanced (relative to the delivery shaft 52) in a proximal-to-distal manner. However, until the detachment shaft 66 and the inflation shaft 54 are advanced (relative to the delivery shaft 52 and the occlusive member 10) in a proximal-to-distal manner, the narrowed portion 70 of the delivery shaft 52 may limit the ability of the occlusive member 10 from exiting the delivery shaft 52.

FIG. 8 further illustrates an example first step in deployment of the occlusive member 10. Specifically, FIG. 8 illustrates blood being sucked into the second lumen (described above) of the inflation shaft 54 (the blood being drawn into the lumen is depicted via the arrow extending through the inflow aperture 68 in FIG. 8). It can be appreciated that this step may be performed by a clinician utilizing a syringe coupled to the second connection port 37 (illustrated and discussed with respect to FIG. 4) to draw a vacuum, and thereby suck blood surrounding the delivery shaft 52 through the inflow aperture 68 and into the second lumen of the inflation shaft 54.

Figure 9:
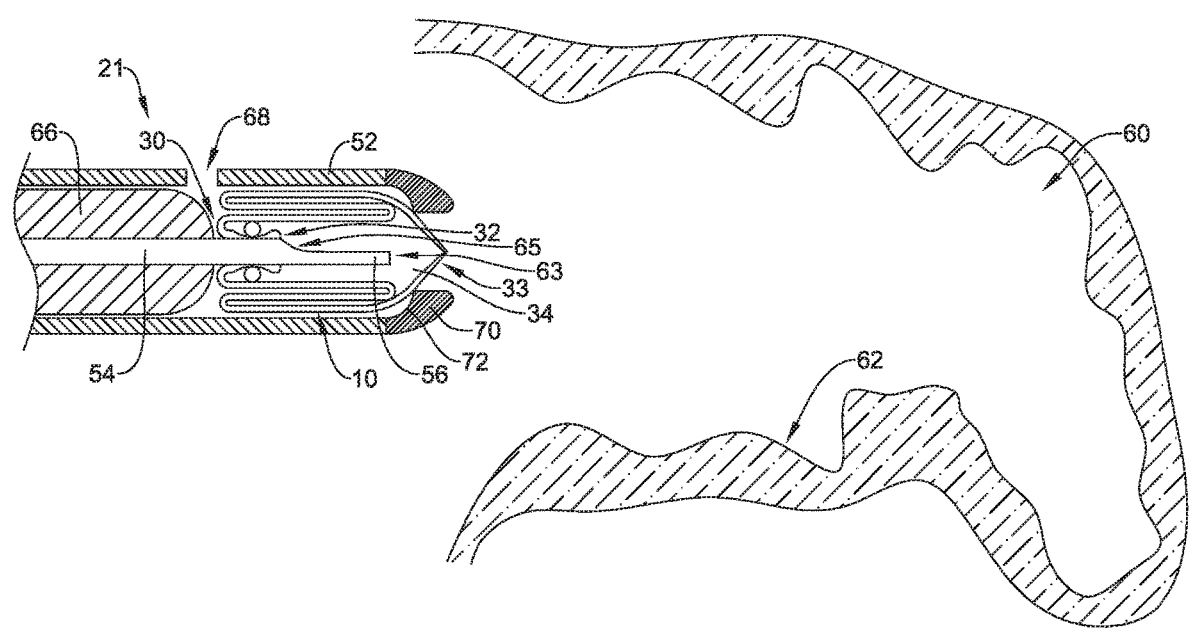

FIG. 9 illustrates an example second step in deployment of the occlusive member 10. FIG. 9 shows the proximal-to-distal advancement of the detachment shaft 66 and the inflation shaft 54 relative to the delivery shaft 52 and the occlusive member 10. It can be appreciated from FIG. 9 that the inflation shaft 54 has been advanced relative to the delivery shaft 52 and the occlusive member 10 to a position in which both the first distal aperture 63 and the second distal aperture 65 are positioned within the inflation cavity 34 of the occlusive member 10. Additionally, FIG. 9 shows that as the detachment shaft 66 and the inflation shaft 54 are advanced distally (relative to the occlusive member 10) the distal end of the detachment shaft 66 may push against the bottom surface 30 of the occlusive member 10. As the detachment shaft 66 pushes against the bottom surface 30 of the occlusive member 10, it may push the apex region 33 toward the distal end of the delivery shaft 52. It should be noted that as the inflation shaft 54 is advanced farther into the inflation cavity 34, the blood which had been drawn in to the second lumen of the inflation catheter may remain in the second lumen. In other words, as the inflation shaft 54 is advanced into the inflation cavity 34, the blood which had been drawn into the inflation shaft 54 (as described above) may eventually be injected into the inflation cavity 34 (which will be described below in greater detail).

Figure 10:
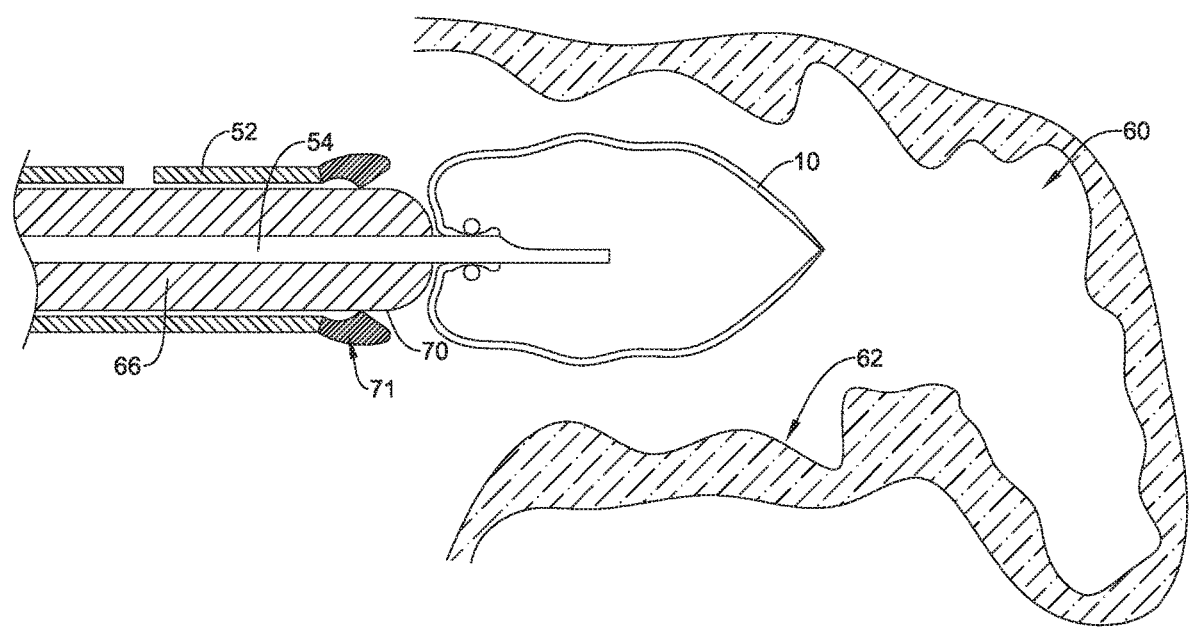

FIG. 10 illustrates an example third step in deployment of the occlusive member 10. Specifically, FIG. 10 illustrates that the proximal-to-distal advancement of the detachment shaft 66 has pushed the occlusive member 10 all the way out of the narrowed portion 70 of the distal end 71 of the delivery shaft 52. As described above, FIG. 10 illustrates that the distal end 71 of the delivery shaft has expanded radially outward to permit the occlusive member 10 and the detachment shaft 66 to pass therethrough. Further, it can be appreciated that the occlusive member 10 shown in FIG. 10 may be in a collapsed (e.g., unexpanded) state and that the first distal aperture 63 and the second distal aperture 65 of the inflation shaft 54 are positioned within the inflation cavity 34.

Figure 11:
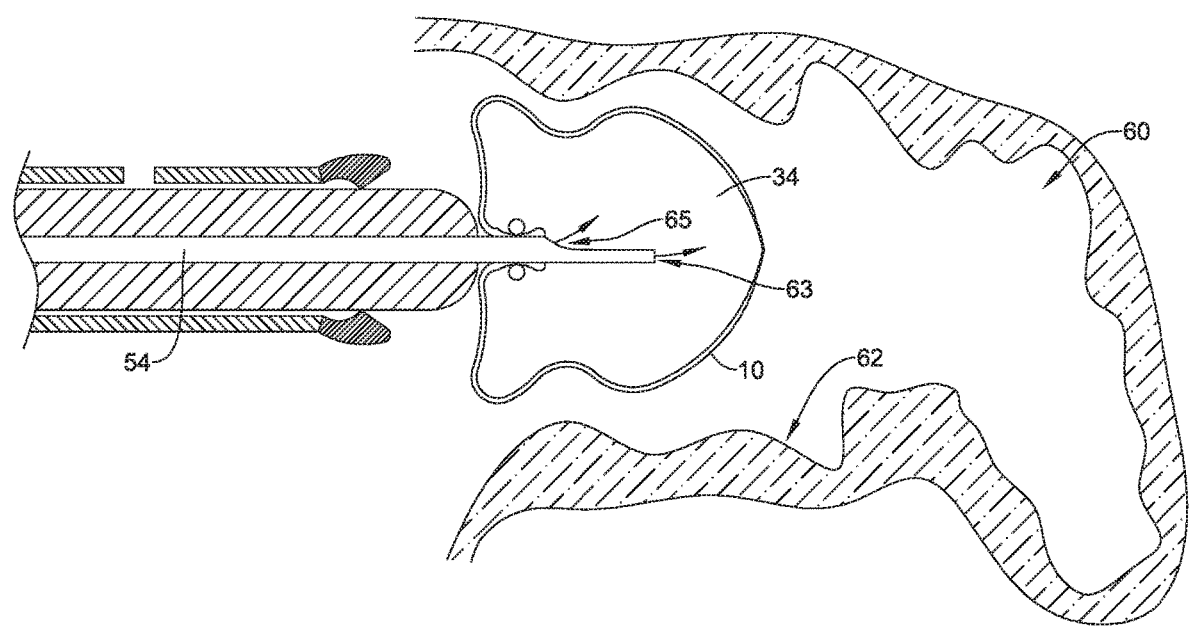

FIG. 11 illustrates an example fourth step in the deployment of the occlusive member 10. Specifically, FIG. 11 illustrates the injection of one or more materials (e.g., fluids, etc.) into the inflation cavity 34 of the occlusive member 10. For example, FIG. 11 illustrates blood (e.g., blood which had been previously drawn into the inflation shaft 54 as described above) being injected into the inflation cavity 34 through the second distal aperture 65 of the second lumen of the inflation shaft 54. Additionally, FIG. 11 illustrates an additional material (e.g., fibrin) being injected into the inflation cavity 34 through the first distal aperture 63 (which is in fluid communication with the first lumen of the inflation catheter described above). Once injected into the inflation cavity 34, the materials (e.g., the blood and fibrin) may be combined to form a semi-solid material as described above. Further, FIG. 11 illustrates the expansion of the expandable member 16 of the occlusive member 10 in response to the injection of the one or more materials into the inflation cavity 34.

Figure 12:
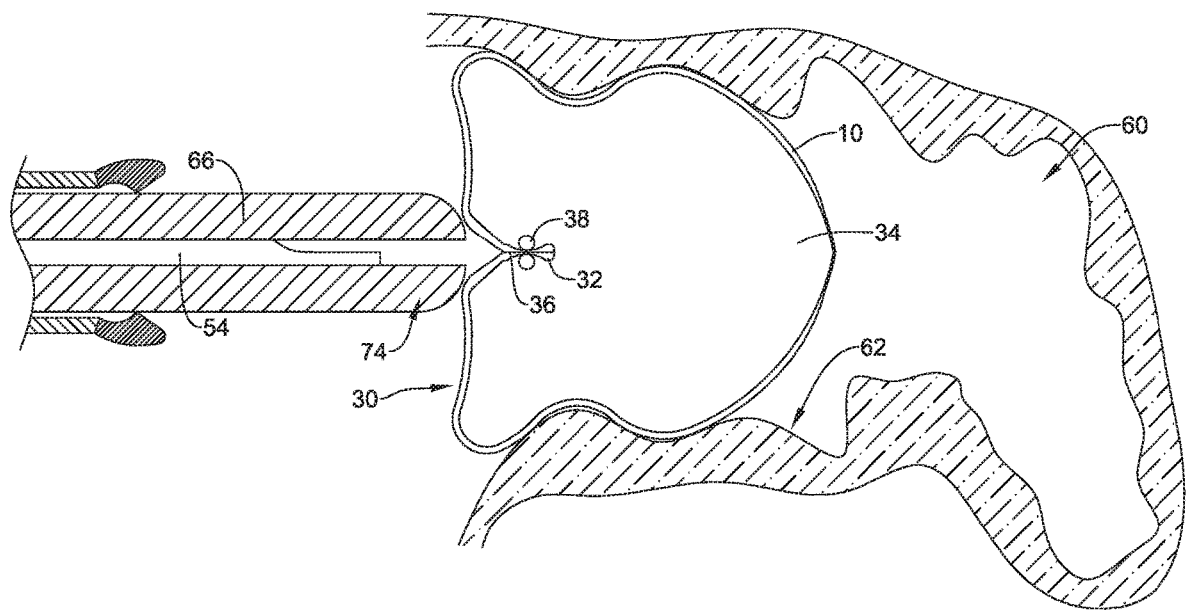

FIG. 12 illustrates an example fifth step in the deployment of the occlusive member 10. Specifically, FIG. 12 illustrates the occlusive member 10 having been expanded to a position in which it seals the opening to the left atrial appendage 60. The seal is formed by the semi-solid material which may be formed by the combining of the one or more materials injected into the inflation cavity 34, as described above. Additionally, FIG. 12 illustrates that the inflation shaft 54 has been withdrawn from the occlusive member 10. Further, in some instances the distal end 74 of the detachment shaft 66 may be positioned against the bottom surface 30 of the occlusive member 10 while the inflation shaft 54 is withdrawn in a distal-to-proximal direction from the occlusive member 10.

Further, it can be appreciated from FIG. 12 that the O-ring 38 has been compressed radially inward to close lumen 36 after the inflation shaft 54 has been removed from the inflation lumen 36 of the valve 32. It can be further appreciated that the O-ring 38 may be designed to exert sufficient force radially inward along the valve 32 to prevent the semi-solid material from passing back through the valve 32 (which may partially collapse the occlusive member 10).

The materials that can be used for the various components of the occlusive member 10 (and variations, systems or components thereof disclosed herein) and the various elements thereof disclosed herein may include those commonly associated with medical devices. For simplicity purposes, the following discussion makes reference to the occlusive member 10 (and variations, systems or components disclosed herein). However, this is not intended to limit the devices and methods described herein, as the discussion may be applied to other elements, members, components, or devices disclosed herein.

In some embodiments, the occlusive member 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive member 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive member 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive member 10 (and variations, systems or components thereof disclosed herein). to achieve the same result.

In some embodiments, a degree of Magnetic Resonance Imaging (MM) compatibility is imparted into the occlusive member 10 (and variations, systems or components thereof disclosed herein). For example, the occlusive member 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive member 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive member 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly praraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive member 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive member 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

While the discussion above is generally directed toward an occlusive member for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A medical device delivery system, comprising:
    an inflation shaft having a first lumen, a second lumen and a distal end region, the distal end region including an elongated tip;
    a detachment shaft extending along a portion of the inflation shaft;
    a delivery shaft having a proximal end region, a distal end region and a lumen extending therein,
    wherein the distal end region of the inflation shaft has a first aperture aligned with the first lumen and a second aperture aligned with the second lumen, and wherein the first aperture is positioned distal to the second aperture,
    wherein the delivery shaft includes a third aperture extending through a wall of the delivery shaft, and wherein the third aperture forms a fluid connection with the second aperture; and
    an occlusive member positioned within at least a portion of the lumen of the delivery shaft;
    wherein the occlusive member is configured to expand and seal the opening of a left atrial appendage;
    wherein a portion of the elongated tip is removeably engaged with the occlusive member.

2. The delivery system of claim 1, wherein the first lumen is radially offset from the second lumen.

3. The delivery system of claim 2, wherein the inflation shaft includes a central longitudinal axis, and wherein the elongated tip is radially offset relative to the longitudinal axis.

4. The delivery system of claim 3, wherein a portion of the elongated tip includes a circular cross-sectional shape.

5. The delivery system of claim 1, wherein the occlusive member includes a valve, and wherein a portion of the elongated tip is releaseably engaged with a portion of the valve.

6. The delivery system of claim 5, wherein the elongated tip is configured to extend through the valve and into an inflation cavity of the occlusive member.

7. The delivery system of claim 1, wherein the inflation shaft is configured to translate relative to the occlusive member such that the first lumen, the second lumen or both the first lumen and second lumen are in fluid communication with an inflation cavity of the occlusive member.

8. The delivery system of claim 7, wherein the first lumen is configured to permit a first fluid to be injected into the inflation cavity of the occlusive member and wherein the second lumen is configured to permit a second fluid to be injected into the inflation cavity of the occlusive member, and wherein the first fluid is configured to combine with the second fluid.

9. The delivery system of claim 8, wherein the first fluid includes blood and wherein the second fluid includes fibrin.

10. The delivery system of claim 1, wherein both the inflation shaft and the detachment shaft extend within a portion of the lumen of the delivery shaft.

11. The delivery system of claim 1, wherein the detachment shaft includes a lumen extending therein and wherein the inflation shaft extends within a portion of the lumen of the detachment shaft.

12. The delivery system of claim 1, wherein the detachment shaft is configured to contact a distal end region of the occlusive member while the inflation shaft is removed from the occlusive member.

13. A method for sealing the left atrial appendage, the method comprising:
    advancing a medical device delivery system to a position adjacent the left atrial appendage, wherein the delivery system includes:
        an inflation shaft having a first lumen, a second lumen and a distal end region, the distal end region including an elongated tip;
        a detachment shaft extending along a portion of the inflation shaft;
        a delivery shaft having a proximal end region, a distal end region and a lumen extending therein; and
        an occlusive member positioned within a portion of the lumen of the delivery shaft;
    inserting a portion of the inflation shaft into an inflation cavity of the occlusive member such that the first lumen and the second lumen are in fluid communication with an inflation cavity;
    injecting a first fluid into the inflation cavity of the occlusive member;
    injecting a second fluid into the inflation cavity such that it combines with the first fluid;
    removing the inflation shaft from the occlusive member.

* * * * *